United States Patent [19]
Jaspers et al.

[11] Patent Number: 5,741,704
[45] Date of Patent: Apr. 21, 1998

[54] HEXOKINASE PROMOTER AND ASSAY METHOD

[75] Inventors: Stephen R. Jaspers, Edmonds; Sherri L. Mudri, Seattle, both of Wash.

[73] Assignee: ZymoGenetics, Inc., Seattle, Wash.

[21] Appl. No.: 580,401

[22] Filed: Dec. 28, 1995

Related U.S. Application Data

[63] Continuation-in-part of Ser. No. 483,212, Jun. 7, 1995, abandoned.

[51] Int. Cl.$^6$ .............................. C12N 5/00; C12N 9/12; C12N 15/09; C07H 21/04
[52] U.S. Cl. .................... 435/325; 435/194; 435/320.1; 536/24.1
[58] Field of Search .................. 435/194, 240.2, 435/320.1, 325; 536/23.5, 24.1

[56] References Cited

PUBLICATIONS

Thelan, "Type II hexokinase" Molecular cloning, sequence and promoter analysis *Diss. Abstr. Int.* 53(7): 3462–B, 1993.
Mathupala et al., *J. Biol. Chem.* 270 (28): 16918–16925, 1995.
Malkki et al., *Biochemical and Biophysical Res. Comm.* 205: 490–496, 1994.
Deeb et al., *Biochemical and Biophysical Res. Comm.* 197: 68–74, 1993.
Printz et al., *J. Biol. Chem.* 268: 5209–5219, 1993.
Postic et al., *Diabetes* 42: 922–929, 1993.
de Wet et al., *Molecular and Cellular Biology* 7: 725–737, 1987.
Guarente et al., *Proc. Natl. Acad. Sci. U.S.A.* 78: 2199–2203, 1981.
Seed et al., *Gene* 67: 271–277, 1988.
Ebina et al., *Cell* 40: 747–758, 1985.
Printz et al. (1995) Diabetes 44, 290–294.

*Primary Examiner*—Rebecca E. Prouty
*Assistant Examiner*—Elizabeth Slobodyansky
*Attorney, Agent, or Firm*—Gary E. Parker

[57] ABSTRACT

Isolated DNA molecules comprising a portion of a human hexokinase gene promoter are disclosed. The molecules comprise promoter and insulin-sensitive transcription regulatory elements. These molecules can be used within methods for detecting insulin-like activity in test substances.

16 Claims, 3 Drawing Sheets

HEXOKINASE PROMOTER AND ASSAY METHOD

CROSS-REFERENCE TO RELATED APPLICATION

This application is a continuation-in-part of Ser. No. 08/483,212, filed Jun. 7, 1995, which application is now abandoned.

BACKGROUND OF THE INVENTION

Diabetes is a major health problem in the western world. The prevalence of the disease in the U.S. is about 6%, and more than 500,000 cases of diabetes are diagnosed each year. Complications of diabetes include blindness, cardiovascular diseases, kidney failure, wound-healing defects (often leading to amputations), and reduced life span.

Diabetes is classified as type I ("insulin-dependent diabetes" or IDDM) or type II ("non-insulin dependent diabetes" or NIDDM). Type I diabetes is believed to arise from autoimmune destruction of insulin-producing pancreatic beta cells. Type II diabetes is characterized by insulin resistance.

Type I diabetes is treated by administration of insulin, which must be injected. Delivery of insulin orally or nasally is not feasible at the present time. Type II diabetes is treated with diet, exercise, and oral hypoglycemic agents (e.g., sulfonylureas). Up to 25% of type II diabetics experience second stage failure and progress to insulin dependence within 5 years of initial diagnosis.

There is a need in the art for improved agents and methods for treating diabetes. There is a further need for therapeutic agents for the treatment of diabetes that can be administered via the mucosa or the gastrointestinal tract. There is also a need for improved methods of identifying such therapeutic agents. The present invention addresses these needs and provides other, related advantages.

SUMMARY OF THE INVENTION

The present invention provides isolated DNA molecules, DNA constructs and cultured mammalian cells, and methods of using these materials within methods for detecting insulin-like activity in test substances.

Within one aspect of the invention there is provided an isolated DNA molecule selected from the group consisting of molecules having a coding strand consisting essentially of nucleotide 17 to nucleotide 2156 Of SEQ ID NO:1; molecules having a coding strand consisting essentially of nucleotide 17 to nucleotide 1790 of SEQ ID NO:1; and allelic variants of (a) and (b), wherein the molecule comprises promoter and insulin-sensitive transcription regulatory elements.

Within a second aspect of the invention there is provided a DNA construct comprising the following operably linked elements: (a) a DNA segment comprising a portion of the sequence of SEQ ID NO:1, or an allelic variant of SEQ ID NO:1, the segment comprising promoter and insulin-sensitive transcription regulatory elements; and (b) a reporter gene. Within certain embodiments of the invention, the DNA segment is selected from the group consisting of segments having a coding strand consisting essentially of nucleotide 17 to nucleotide 2156 of SEQ ID NO:1; segments having a coding strand consisting essentially of nucleotide 17 to nucleotide 1790 of SEQ ID NO:1; and allelic variants of (a) and (b). Within a related aspect of the invention, the DNA segment is a segment having a coding strand consisting essentially of nucleotide 17 to nucleotide 2155 of SEQ ID NO:1 or an allelic variant thereof. Within another related aspect of the invention, the DNA segment is selected from the group consisting of (a) segments having a coding strand consisting of nucleotide 12 to nucleotide 2156 of SEQ ID NO:1, (b) segments having a coding strand consisting of nucleotide 12 to nucleotide 2155 of SEQ ID NO:1, (c) segments having a coding strand consisting of nucleotide 12 to nucleotide 1790 of SEQ ID NO:1, and (d) allelic variants of (a), (b), and (c).

Within another embodiment of the invention, the reporter gene is selected from the group consisting of luciferase, β-galactosidase and chloramphenicol acetyltransferase genes. Within a further embodiment of the invention, a TATA sequence heterologous to the DNA segment is positioned between the DNA segment and the reporter gene.

Within a third aspect of the invention there is provided a cultured mammalian cell containing a DNA construct as disclosed above, wherein the reporter gene is expressed in the cell and the cell further comprises an expressed hexokinase II gene. Within one embodiment of the invention, the cell is a muscle or adipocyte cell having a differentiated phenotype when cultured in vitro.

Within a related aspect of the invention, a cultured mammalian cell as disclosed above is cultured in the presence and absence of a test substance, and expression of the reporter gene is measured, wherein an increase in expression of the reporter gene in the presence of the test substance is indicative of insulin-like activity in the test substance. Within one embodiment of the invention, a test substance having insulin-like activity as determined by an increase in expression of the reporter gene in the presence of the test substance is further tested in a second assay for insulin-like activity, such as an assay measuring stimulation of glucose transport in test cells. Within a further aspect of the invention, the test substance is one that has been previously found to bind to cell-surface insulin receptors and thereby induce signal transduction in a target cell.

These and other aspects of the invention will become evident upon reference to the following detailed description of the invention and the attached drawings.

DETAILED DESCRIPTION OF THE INVENTION

Figure 1:
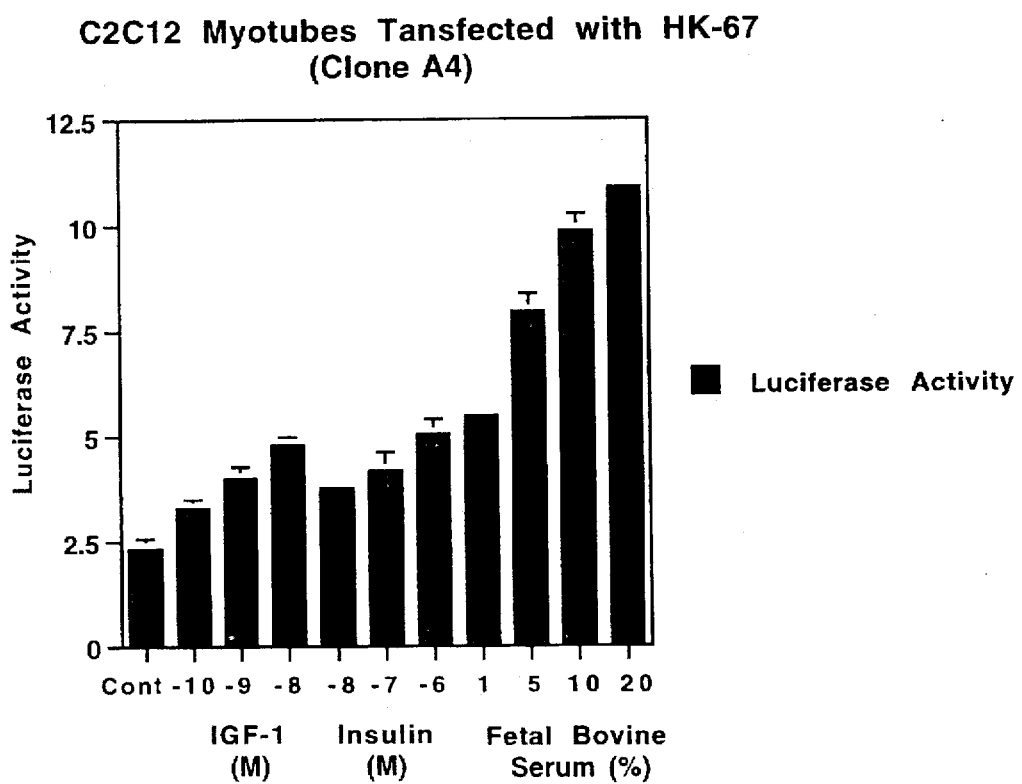
FIG. 1 illustrates the results of a luciferase activity assay on transfected C2C12 myotubes. The cells were stimulated with concentrations of IGF-1, insulin or fetal bovine serum as shown. Cont=control.

The term "allelic variant" is used herein to denote an alternative form of a gene. Allelic variation is known to exist in populations and arises through mutation.

The term "coding strand" is used for its conventional meaning to denote the strand of a double-stranded DNA molecule that does not serve as a template for transcription.

A "DNA construct" is a DNA molecule, either single- or double-stranded, that has been modified through human intervention to contain segments of DNA combined and juxtaposed in an arrangement not existing in nature.

The term "gene" is used herein to denote a DNA segment encoding a polypeptide, and includes genomic DNA (with or without intervening sequences), cDNA, and synthetic DNA. Genes may include non-coding sequences, including promoter elements.

"Operably linked", when referring to DNA segments, indicates that the segments are arranged so that they function in concert for their intended purposes, e.g. transcription initiates in the promoter and proceeds through the coding segment to the terminator.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "promoter elements" is used to denote sequences within promoters that function in the initiation of transcription and which are often characterized by consensus nucleotide sequences. Promoter elements include RNA polymerase binding sites; TATA sequences; CAAT sequences; differentiation-specific elements (DSEs; McGehee et al., *Mol. Endocrinol.* 7:551–560, 1993); cyclic AMP response elements (CREs); serum response elements (SREs; Treisman, *Seminars in Cancer Biol.* 1:47–58, 1990); glucocorticoid response elements (GREs); and binding sites for other transcription factors, such as CRE/ATF (O'Reilly et al., *J. Biol. Chem.* 267:19938–19943, 1992), AP2 (Ye et al., *J. Biol. Chem.* 269:25728–25734, 1994), SP1, cAMP response element binding protein (CREB; Loeken, *Gene Expr.* 3:253–264, 1993) and octamer factors. See, in general, Watson et al., eds., *Molecular Biology of the Gene*, 4th ed., The Benjamin/Cummings Publishing Company, Inc., Menlo Park, Calif., 1987; and Lemaigre and Rousseau, *Biochem. J.* 303:1–14, 1994.

"Transcription regulatory elements" are promoter-associated DNA sequences that bind regulatory molecules, resulting in the modulation of the frequency with which transcription is initiated. Transcription regulatory elements can be classified as enhancers or suppressors of transcription.

The term "reporter gene" is used herein to denote a gene that, when expressed in a cell, produces a quantifiable phenotypic change in the cell. Preferred reporter genes include genes encoding enzymes. Particularly preferred enzymes are luciferase, β-galactosidase, and chloramphenicol acetyltransferase. Assays for these enzymes are known in the art. See, for example, Seed and Sheen, *Gene* 67:271–277, 1988; Todaka et al., *J. Biol. Chem.* 269:29265–29270, 1994; Guarente et al., *Proc. Natl. Acad. Sci. USA* 78:2199–2203, 1981; Mellon et al. *Proc. Natl. Acad. Sci. USA* 86:4887–4891, 1989; and Brasier et al., *BioTechniques* 7:1116–1122, 1989, which are incorporated herein by reference in their entirety. Reporter genes, assay kits, and other materials are available commercially from suppliers such as Promega Corp. (Madison, Wis.) and GIBCO BRL (Gaithersburg, Md.).

The present invention provides an isolated human hexokinase II (HKII) gene segment comprising promoter and insulin-sensitive transcription regulatory elements. This HKII gene segment can be used within methods of detecting insulin-like activity in a test substance, and is therefore a valuable tool for use by the pharmaceutical industry for drug discovery and development.

A representative HKII gene segment is shown in SEQ ID NO:1. Those skilled in the art will recognize that the illustrated sequence is but one allele of the human HKII gene, and that allelic variants of this sequence would be expected to exist. Allelic variants can be obtained by cloning from DNA libraries derived from other individuals and can be used within the present invention.

Analysis of the sequence shown in SEQ ID NO:1 revealed the presence of a number of promoter elements within the ca. 2.1 kb 5'-flanking region of the human HKII gene. These include a DSE-like sequence at nucleotides 308–321; a CRE sequence at 471–478; CAAT box sequences at 569–574 and 1644–1648; a C/EBP element at 728–737; SP1 binding site elements at 1608–1612, 1619–1623, 1649–1653, and 1999–2003 on the coding strand and on the non-coding strand at positions complementary to nucleotides 1498–1502, 1509–1513, 1516–1520, and 2095–2099; and an AP2 site at 1532–1539.

Preferred portions of the sequence shown in SEQ ID NO:1 for use within the present invention include segments having a coding strand consisting essentially of nucleotide 17 to nucleotide 2156 of the sequence shown in SEQ ID NO:1 and segments having a coding strand consisting essentially of nucleotide 17 to nucleotide 1790 of SEQ ID NO:1. Those skilled in the art will recognize that portions of SEQ ID NO:1 having 3' termini intermediate to those of these preferred portions are also useful within the present invention. When using a segment having a coding strand consisting essentially of nucleotide 17 to nucleotide 1790 of SEQ ID NO:1 it is preferred to combine it with a TATA box sequence, such as a TATA box sequence from a gene other than HKII. The TATA box sequence will be positioned between the HKII promoter sequence and the reporter gene. The term "consisting essentially of" is used herein to include segments having minor 5' or 3' terminal extensions that do not affect their biological function, particularly extensions of up to about 20 nucleotides, preferably 10 or fewer nucleotides, that provide restriction enzyme cleavage sites to facilitate cloning and other manipulation of DNA fragments. For example, a convenient restriction site (Sac II; GAGCTC) occurs at nucleotides 12–17 of SEQ ID NO:1. Those skilled in the art will recognize that smaller portions of a human HKII gene promoter can also be utilized within the present invention. For example, a DNA segment consisting of nucleotides 12–2155 of SEQ ID NO:1 is equivalent to a segment consisting of nucleotides 12 (or 17) through 2156. The exact termini of segments employed in DNA constructs of the present invention will be determined in part by the selection of restriction endonucleases, PCR primers and other routine design considerations. Minor variations will not generally have a significant effect upon the utility of a particular segment as long as important promoter elements are retained. Such smaller portions can be readily identified by joining them to a reporter gene and assaying for insulin-sensitive expression.

A DNA segment comprising a portion of the sequence of SEQ ID NO:1, or an allelic variant of SEQ ID NO:1, as disclosed above and including promoter and insulin-sensitive transcription regulatory elements, is joined to a reporter gene to provide an insulin-sensitive reporter element. The insulin-sensitive reporter element is incorporated into an expression vector, which is in turn introduced into a host cell. In general, the expression vector will include promoter (including, but not limited to, the HKII sequences), terminator and polyadenylation sequences required for expression of the reporter gene. The vector may also include one or more origins of replication that allow for its maintenance and amplification in alternate hosts, one or more selectable markers, etc. A selectable marker may also be introduced into the host cell on an unlinked construct by co-transfection. Methods for introducing exogenous DNA molecules into cultured cells and culturing the cells so that the introduced molecules are expressed are well known in the art. See, for example, Sambrook et al., *Molecular Cloning: A Laboratory Manual*, 2nd ed., Cold Spring Harbor Laboratory Press, Cold Spring Harbor, N.Y., 1989; Ausubel et al., eds., *Current Protocols in Molecular Biology*, John Wiley and Sons, Inc., NY, 1987; Wigler et al., *Cell* 14:725, 1978; Corsaro and Pearson, *Somatic Cell Genetics* 7:603, 1981; Graham and Van der Eb, *Virology* 52:456, 1973; Neumann et al., *EMBO J.* 1:841–845, 1982; Hagen et al., U.S. Pat. No. 4,784,950; and Palmiter et al., U.S. Pat. No. 4,579,821, which are incorporated herein by reference in their entirety.

Host cells suitable for use within the present invention include mammalian cells that can be grown in culture and produce hexokinase II. Of particular interest are muscle and adipocyte cell lines that exhibit a differentiated phenotype in vitro. Differentiated muscle and adipocyte cell lines are characterized by insulin-sensitive glucose metabolism. Preferred muscle cell lines include C2C12 (ATCC CRL 1772), a mouse myoblast cell line; L6 (ATCC CRL 1458), a rat skeletal muscle myoblast cell line; H9c2(2-1) (ATCC CRL 1446), a rat heart myoblast cell line; and $BC_3H1$ (ATCC CRL 1443), a smooth muscle-like cell line from mouse brain tumor. Preferred adipocyte cell lines include 3T3-L1 (ATCC CCL 92.1), a mouse embryonic cell line; and 3T3-F442A, a mouse preadipocyte/adipocyte cell line (Printz et al., *J. Biol. Chem.* 268:5209–5219, 1993).

Cells transfected with a DNA construct comprising an insulin-sensitive reporter element as disclosed above are maintained in conventional culture media. Media selection is determined by the needs of the particular host cells and is within the level of ordinary skill in the art. Culture media for mammalian cell lines are typically buffered solutions containing a carbon source, nitrogen source, salts, growth factors and antibiotics. Some of the required components can be supplied by serum (e.g. fetal bovine serum).

The transfected cells are used within assay systems to detect the presence of insulin-like activity in a test substance. General methods for detecting the activity of a reporter gene are known in the art, and assay kits, reagents, and instruments are commercially available.

Within one embodiment of the invention, the reporter gene is a luciferase gene, and the host cells are C2C12 myoblasts. These cells are maintained in Dulbecco's minimum essential media (DMEM) containing 4.5 g glucose/liter, 20 mM Hepes, 2 mM 1-glutamine, 10% fetal bovine serum (FBS) and 1 mg/ml Geneticin (G418) (or other appropriate selective agent). Media components can be purchased from commercial suppliers (e.g. GIBCO BRL, Gaithersburg, Md.). To assay for insulin-like activity, transfected cells are seeded in suitable assay plates (e.g. 96-well Microlite™ tissue culture plates (Dynatech Laboratories, Inc., Chantilly, Va.)) and allowed to grow to confluence. The cells are induced to differentiate by placing them in DMEM containing 20 mM Hepes, 2 mM 1-glutamine and 2% horse serum for 3–8 days. One to two days prior to assay, the medium is changed to serum-free DMEM containing 0.5% bovine serum albumin (BSA) and the appropriate concentration of hormone (e.g. insulin or IGF-1) or serum, or multiple dilutions of test substance. In general, standards are applied at concentrations within which a cellular response can be obtained, so that when using insulin or IGF-1, these substances will be included in the medium at $10^{-12}$ to $10^{-6}$M. The test substances are included through a dilution range to obtain a measurable response. The cells are maintained at 37° C. in a 95% air:5% $CO_2$ incubator for approximately five hours. The cells are then rinsed with phosphate buffered saline (PBS) and lysed with 25 μl Cell Culture Lysis buffer (Luciferase Detection Kit #E1500 or #E1501; Promega Corp., Madison, Wis). Luciferase activity is measured using the reagent in the detection kit and a suitable luminometer (e.g. Luminoskan™ luminometer, ICN Biomedical, Cleveland, Ohio). Results of assays on test samples are compared to a standard curve prepared using purified standards (insulin or IGF-1).

Within an alternative embodiment, L6 myoblasts transfected with the luciferase reporter construct are maintained in DMEM containing 1 g glucose/liter, 20 mM Hepes, 2 mM 1-glutamine, 10% FBS and 1 mg/ml G418 (or other appropriate selective agent). Cells are induced to differentiate into myotubes by culturing in the same medium containing only 0.5–1.0% FBS and supplemented with 5 μg/ml insulin. Differentiation occurs within 10–14 days. The cells are then used within the assay system described above.

Samples testing positive for insulin activity in a primary screen, such as one of the luciferase activity assays described above, can be further tested in one of a number of secondary assays for insulin-like activity. Such secondary assays include, for example, assays of insulin-stimulated glucose transport (as disclosed by, for example, Manchester et al., *Am. J. Physiol.* 266 (*Endocrinol. Metab.* 29):E326–E333, 1994); insulin-stimulated lipogenesis, such as by measuring the incorporation of $^{14}C$-acetate into triglyceride (Mackall et al. *J. Biol. Chem.* 251:6462–6464, 1976) or triglyceride accumulation (Kletzien et al., *Mol. Pharmacol.* 41:393–398, 1992); glycogen synthesis (as disclosed by, for example, Verspohl et al., *J. Clin. Invest* 74:1436–1443, 1984), and other measurements of known insulin activities. A preferred secondary assay is an assay for insulin-stimulated glucose transport. Non-transfected, differentiated L6 myotubes (produced as described above and maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^3H$ or $^{14}C$-labeled deoxyglucose is added to ≈50 μM final concentration, and the cells are incubated for approximately 10–30 minutes. The cells are then quickly rinsed with cold buffer (e.g. PBS), then lysed with a suitable lysing agent (e.g. 1% SDS or 1N NaOH). The cell lysate is then evaluated by counting in a scintillation counter. Cell-associated radioactivity is taken as a measure of glucose transport after subtracting non-specific binding as determined by incubating cells in the presence of cytocholasin b, an inhibitor of glucose transport.

In the alternative, the HKII promoter-based methods can be used as secondary screens to assay compounds showing insulin-like activity in a primary assay that detects insulin-signaling activity in a test compound. Primary assays of this type are based on binding of a test compound to cell-surface insulin receptors and consequent induction of signal transduction in a target cell. A variety of such assays are available, and can employ cells expressing endogenous insulin receptors or cells expressing cloned, heterologous insulin receptors. One such assay is a glucose transport assay as disclosed above. A second such assay is a mitogenesis assay using insulin-responsive cells. A third such assay measures insulin-dependent expression of a reporter gene, such as a luciferase gene. Within this type of assay, cells are transfected with an insulin-responsive reporter gene construct, typically a serum response element (SRE) linked to a reporter gene according to conventional methods. As noted above, the cell can be one that expresses an endogenous insulin receptor or one that is transfected to express a heterologous receptor. Cells of the latter type provide certain advantages, including the use of well-characterized cell lines (e.g., baby hamster kidney cell lines) that are commonly used in laboratory and large-scale systems for the production of recombinant proteins.

The invention is further illustrated by the following, non-limiting examples.

EXAMPLES

Example 1

Six human genomic clones were obtained from Genome Systems, Inc. (St. Louis, Mo.). The clones were identified in the Du Pont Merck Pharmaceutical Company Human Foreskin Fibroblast P1 Library #1 (DMPC-HFF#1) (see, *The P1 Manual*, Genome Systems, Inc., 1994; and Sternberg, *Proc. Natl. Acad. Sci. USA* 87:103–107, 1990) by screening using oligonucleotides 7898 (SEQ ID NO:2) and 7900 (SEQ ID NO:3). The clones were supplied in *E. coli* strain NS 3529.

A 132 bp PCR fragment corresponding to a region of hexokinase exon 1 (Deeb et al., *Biochem. Biophys. Res. Comm.* 197:68–74, 1993) was used to probe a Sac I digest of the six clones. Four of the clones contained a hybridizing Sac I band of approximately 2.2 kb. The other two clones were determined to be HKII pseudogene clones.

A 2.2 kb Sac I fragment comprising HKII promoter sequence was isolated from one of the clones (library plate 66, well G12; designated DMPC-HFF#1-0066G) and ligated to the vector pBS-Sst I (Stratagene Cloning Systems, La Jolla, Calif.). The resulting construct was designated pBS-P1.Sst. The HKII region of the construct was sequenced to confirm its identity. The 2.2 kb HKII fragment was re-isolated from the vector as a Kpn I-Eco RI fragment by cleaving polylinker sites in the vector.

The HKII fragment was joined to a luciferase gene in the plasmid pKZ67. This plasmid is a pUC18-derived mammalian cell expression vector comprising a luciferase expression unit that includes a synthesized segment containing human c-fos sequence from −360 to +30 (van Straaten et al., *Proc. Natl. Acad. Sci. USA* 80:3183–3187, 1983) (including TATA, SRE and SIE promoter elements), a luciferase sequence (Delegeane et al., *Mol. Cell Biol.* 7:3994–4002, 1987; deWet et al., *Mol. Cell. Biol.* 7:725–737, 1987), and a human growth hormone gene terminator. This expression unit is in opposite transcriptional orientation to a second expression unit that includes a neomycin resistance marker flanked by SV40 prompter and terminator sequences.

The 2.2 kb HKII promoter fragment was treated with DNA polymerase I Klenow fragment to fill in (blunt) the Eco RI end. The blunted fragment was inserted into plasmid pKZ67 that had been digested with Kpn I and Bam HI and treated with DNA polymerase I Klenow fragment to blunt the Bam HI end. This construction joined the HKII fragment to the luciferase sequence in pKZ67, deleting the plasmid SRE and TATA box. The resulting construct was designated HK67.

C2C12 and L6 myoblasts were transfected with plasmid HK67. C2C!2 myoblasts were maintained in DMEM containing 4.5 g glucose/liter, 20 mM Hepes, 2 mM l-glutamine, 10% fetal bovine serum (FBS) and 1 mg/ml G418. Transfected L6 myoblasts were maintained in DMEM containing 1 g glucose/liter, 20 mM Hepes, 2 mM l-glutamine, 10% FBS and 1 mg/ml G418.

To assay for insulin-like activity, transfected C2C12 cells were seeded in 96-well Microlite™ tissue culture plates (Dynatech Laboratories, Inc., Chantilly, Va.) and allowed to grow to confluence. The cells were induced to differentiate by placing them in DMEM containing 20 mM Hepes, 2 mM l-glutamine and 2% horse serum for 3–8 days. One to two days prior to assay, the medium was changed to serum-free DMEM containing 0.5% bovine serum albumin (BSA), and dilutions of insulin ($10^{-6}$, $10^{-7}$ and $10^{-8}$M), IGF-1 ($10^{-8}$, $10^{-9}$ and $10^{-10}$M) and FBS (1%, 5%, 10% and 20%) were added. The cells were maintained at 37° C. in a 95% air:5% $CO_2$ incubator for approximately five hours, then rinsed with PBS and lysed with 25 µl Cell Culture Lysis buffer (Luciferase Detection Kit #E1500 or #E1501; Promega Corp., Madison, Wis.). Luciferase activity was measured using the reagent in the detection kit and a Luminoskan™ luminometer (ICN Biomedical, Cleveland, Ohio). Results of the assays are shown in FIG. 1.

A second assay was performed on a second clonal isolate of C2C12 transfectants. Cells were cultured and differentiated as described above, then cultured in serum-free DMEM+0.5% BSA supplemented with insulin ($10^{-6}$, $10^{-7}$ and $10^{-8}$M) or FBS (1%, 5%, 10% and 20%). Results of the assays are shown in FIG. 2.

L6 myoblasts were induced to differentiate into myotubes by culturing in DMEM containing 1 g/l glucose, 20 mM Hepes, 2 mM l-glutamine, 0.5–1.0% FBS, 1 mg/ml G418 and 5 µg/ml insulin. Differentiation occured within 10–14 days. The cells were then used within the assay system described above, using insulin at $10^{-11}$ to $10^{-6}$M and FBS at 1%, 5%, 10% and 20%. Results are shown in FIG. 3.

Figure 2:
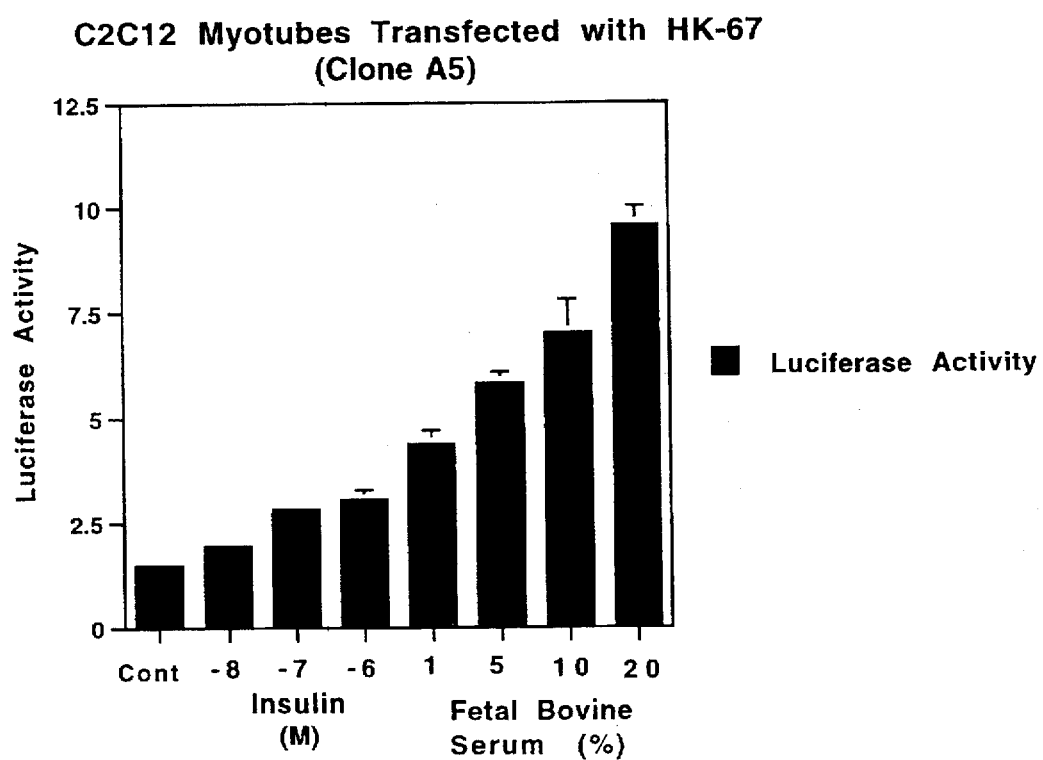
FIG. 2 illustrates the results of a luciferase activity assay on transfected C2C12 myotubes stimulated with insulin or fetal bovine serum at the noted concentrations. Cont=control.
Figure 3:
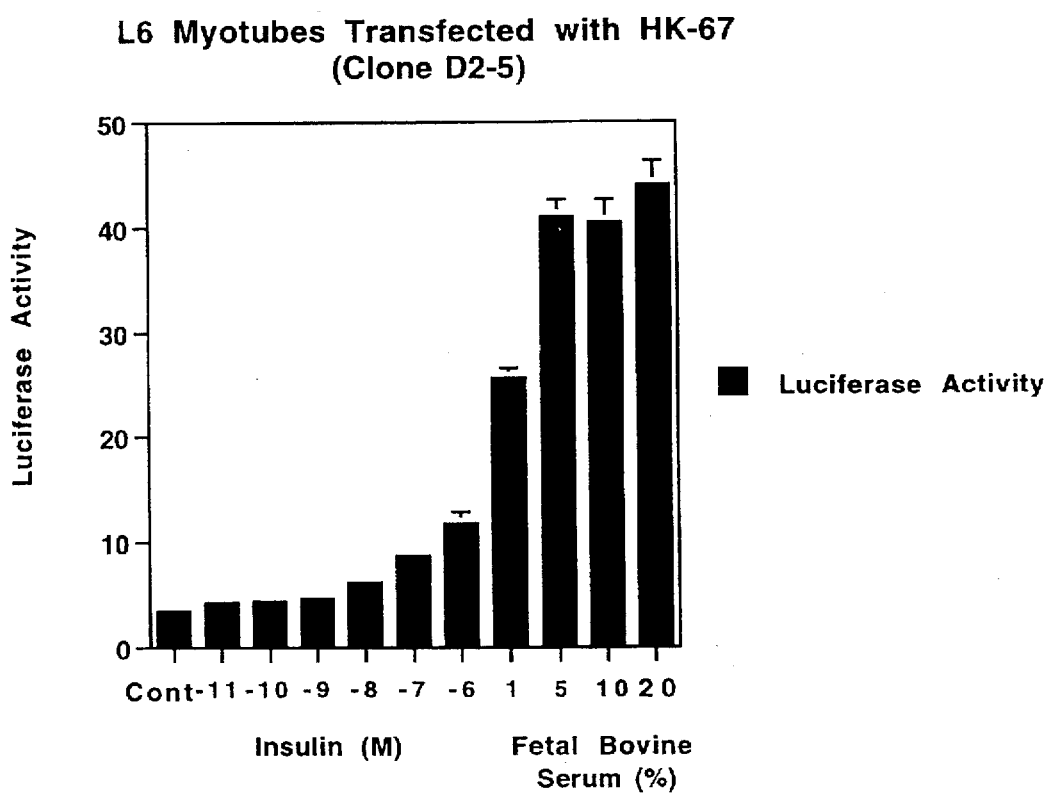
FIG. 3 illustrates the results of a luciferase activity assay on transfected L6 myotubes stimulated with insulin or serum at the noted concentrations. Cont=control.

The assay results shown in FIGS. 1–3 demonstrated that luciferase activity in the C2C12 and L6 transfectants was responsive to insulin and serum, and that C2C12 transfectants were also sensitive to IGF-1. Levels of induction (or de-repression) were lower than desired. Further analysis of HK67 indicated that the fusion of the HKII ATG and 39 bases of exon 1 coding sequence to the luciferase sequence could alter the reading frame and adversely affect luciferase activity, resulting in a greatly reduced insulin response.

Example 2

A second reporter plasmid was constructed using a truncated ≈1.8 kb HKII promoter fragment that was isolated from pBS-P1.Sst as a Kpn I-Apa I fragment. The Apa I end was filled in (blunted) using DNA polymerase I Klenow fragment. This 1.8 kb fragment lacked the HKII ATG and exon 1 sequence, and spanned the region from nucleotide 12 to nucleotide 1790 of SEQ ID NO:1. The 1.8 kb fragment was ligated to pKZ67 that had been digested with Kpn I and Xho I (blunted). The resulting construct was designated HKAX, and comprised the 1.8 kb HKII promoter fragment, a TATA sequence from the pKZ67 parent vector, and the luciferase reporter gene.

Example 3

Two additional HKII promoter/luciferase reporter constructs were prepared. These constructs were designated pKZSB#12 and pKZSX#11. Both contained the HKII promoter sequence from nucleotide 12 to nucleotide 2155 (SEQ ID NO:1). In pKZSB#12 the HKII promoter was cloned into a pKZ67 backbone at the Kpn I and Bam HI sites, resulting in deletion of the plasmid TATA box. In pKZSX#11 the HKII promoter was cloned into a pKZ67 backbone at the Kpn I and Xho I sites, retaining the plasmid TATA box.

The 5' portion of the HKII promoter was obtained from pBS-P1.Sst by digesting the plasmid with Kpn I and Apa I. A fragment comprising the 5' end of the HKII promoter was isolated by gel electrophoresis.

The 3' portion of the HKII promoter was generated by PCR using Kpn I-linearized HK67 plasmid as template. Oligonucleotide 9416 (SEQ ID NO:4), which corresponds to HKII sequence at nucleotides 1745–1764 of SEQ ID NO:1, was paired with each of oligonucleotides 9389 (SEQ ID NO:5) and 9390 (SEQ ID NO:6), which correspond to HKII sequence at nucleotides 2140–2157 of SEQ ID NO:1. The reaction mixture contained 10 μl of 10×reaction buffer (Boehringer Mannheim, Indianapolis, Ind.), 1 μl of 20 mM dNTP mix (Pharmacia Biotech, Piscataway, N.J.), 5 μl of each oligonucleotide (20 pmol/ml), 10 μl template DNA (10 ng/μl), 1 μl of Taq DNA polymerase (Boehringer Mannheim), 8 μl of DMSO and 60 μl of $H_2O$. The reaction was run using the "hot start" method with wax beads (AmpliWax®, Perkin Elmer, Foster City, Calif.). Reaction products were extracted with phenol:chloroform, digested with restriction enzymes (Apa I+Bam HI or Apa I+Xho I, as appropriate), and separated on 2% agarose gels. DNA bands were isolated using a Gene Clean kit (Bio101, La Jolla, Calif.). Two 413 bp fragments were obtained, one of which included a 3' Bam HI site, the other of which included a 3' Xho I site.

Plasmid pKZSB#12 was generated by ligating the Kpn I-Bam HI vector fragment of pKZ67 with the 1800 bp 5' HKII promoter fragment and the 413 bp Apa I-Bam HI PCR fragment using DNA ligase and 10×ligase buffer from Gibco BRL (Gaithersburg, Md.).

Plasmid pKZSX#11 was generated by ligating the Kpn I-Xho I vector fragment of pKZ67 with the 1800 bp 5' HKII promoter fragment and the 413 bp Apa I-Xho I PCR fragment.

The two plasmids were electroporated into *E. coli* DH10B cells, and colonies were screened by restriction digest analysis. Positive clones were picked, and plasmid DNA was prepared and sequenced.

Sequence-confirmed DNA of plasmids pKZSB#12 and pKZSX#11 was used to transfect C2C12 cells. Thirty clones of each transfectant were selected in G418, grown to confluence, differentiated, and assayed for insulin responsiveness as described above. Both constructs were essentially the same in their ability to induce luciferase expression in response to insulin or FBS (Table). However, cells transfected with pKZSX#11, which contains the TATA box, were better able to survive differentiation and down-regulation in serum-free medium. The presence of myotubes did not appear to significantly affect the induction of luciferase activity.

TABLE

| Plasmid | Basal Activity | Fold Induction | |
|---|---|---|---|
| | | Insulin | FBS |
| pKZSB#12 | 22.5 | 1.44 | 1.98 |
| pKZSX#11 | 22.3 | 1.29 | 2.03 |

Data are averages of 29 clones assayed.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated DNA molecule selected from the group consisting of:

(a) molecules having a coding strand consisting of from 2140 to 2180 nucleotides and comprising nucleotide 17 to nucleotide 2156 of SEQ ID NO:1;

(b) molecules having a coding strand consisting of from 1774 to 2014 nucleotides and comprising nucleotide 17 to nucleotide 1790 of SEQ ID NO:1; and (c) allelic variants of (a) and (b), wherein said molecule comprises promoter and insulin-sensitive transcription regulatory elements.

2. A DNA construct comprising the following operably linked elements:

a DNA segment comprising a portion of the sequence of SEQ ID NO:1, or an allelic variant of SEQ ID NO:1, said segment comprising promoter and insulin-sensitive transcription regulatory elements; and a reporter gene, wherein the reporter gene is not a hexokinase gene.

3. A DNA construct according to claim 2 wherein said DNA segment is selected from the group consisting of:

(a) segments having a coding strand consisting of from 2140 to 2180 nucleotides and comprising nucleotide 17 to nucleotide 2156 of SEQ ID NO:1;

(b) segments having a coding strand consisting of from 1774 to 2014 nucleotides and comprising nucleotide 17 to nucleotide 1790 of SEQ ID NO:1; and (c) allelic variants of (a) and (b).

4. A DNA construct according to claim 2 wherein said DNA segment is a segment having a coding strand consisting of from 2139 to 2179 nucleotides and comprising nucleotide 17 to nucleotide 2155 of SEQ ID NO:1 or an allelic variant thereof.

5. A DNA construct according to claim 2 wherein said DNA segment is selected from the group consisting of:

(a) segments having a coding strand consisting of nucleotide 12 to nucleotide 2156 of SEQ ID NO:1;

(b) segments having a coding strand consisting of nucleotide 12 to nucleotide 2155 of SEQ ID NO:1;

(c) segments having a coding strand consisting of nucleotide 12 to nucleotide 1790 of SEQ ID NO:1; and (d) allelic variants of (a), (b), and (c).

6. A DNA construct according to claim 2 wherein the reporter gene is selected from the group consisting of luciferase, β-galactosidase and chloramphenicol acetyltransferase genes.

7. A DNA construct according to claim 2 wherein the reporter gene is a luciferase gene.

8. A DNA construct according to claim 2 further comprising a TATA sequence heterologous to the DNA segment positioned between the DNA segment and the reporter gene.

9. A cultured mammalian cell containing a DNA construct comprising the following operably linked elements:

a DNA segment comprising a portion of the sequence of SEQ ID NO:1, or an allelic variant of SEQ ID NO:1, said segment comprising promoter and insulin-sensitive transcription regulatory elements; and a reporter gene, wherein the reporter gene is not a hexokinase gene and wherein the reporter gene is expressed in the cell and the cell further comprises an expressed hexokinase II gene.

10. A cultured mammalian cell according to claim 9 wherein said DNA segment is selected from the group consisting of:
   (a) segments having a coding strand consisting of from 2140 to 2180 nucleotides and comprising nucleotide 17 to nucleotide 2156 of SEQ ID NO:1;
   (b) segments having a coding strand consisting of from 1774 to 2014 nucleotides and comprising nucleotide 17 to nucleotide 1790 of SEQ ID NO:1; and
   (c) allelic variants of (a) and (b).

11. A cultured mammalian cell according to claim 9 wherein said DNA segment is a segment having a coding strand consisting of from 2139 to 2179 nucleotides and comprising nucleotide 17 to nucleotide 2155 of SEQ ID NO:1 or an allelic variant thereof.

12. A cultured mammalian cell according to claim 9 wherein said DNA segment is selected from the group consisting of:
   (a) segments having a coding strand consisting of nucleotide 12 to nucleotide 2156 of SEQ ID NO:1;
   (b) segments having a coding strand consisting of nucleotide 12 to nucleotide 2155 of SEQ ID NO:1;
   (c) segments having a coding strand consisting of nucleotide 12 to nucleotide 1790 of SEQ ID NO:1; and
   (d) allelic variants of (a), (b), and (c).

13. A cultured mammalian cell according to claim 9 wherein the reporter gene is selected from the group consisting of luciferase, $\beta$-galactosidase and chloramphenicol acetyltransferase genes.

14. A cultured mammalian cell according to claim 9 wherein the reporter gene is a luciferase gene.

15. A cultured mammalian cell according to claim 9 which is a muscle or adipocyte cell having a differentiated phenotype when cultured in vitro.

16. A cultured mammalian cell according to claim 9 wherein said DNA construct further comprises a TATA sequence heterologous to the DNA segment positioned between the DNA segment and the reporter gene.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
 ( A ) LENGTH: 2201 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:1:

```
TCTGACCTCT  GGAGCTCAAT  TCTGTGTGGA  GTATAGGGAA  GGAGGGTTGA  GGACGTGCAT    60

TTAGAAGGGT  ACATAGTTCT  CAAGAAGTTT  TGCTGAGCAC  ATCTGTAATC  CCAGCTATTT   120

GGGACGCTGA  AGTGGGAGGA  CTGCTTGAGC  CCAGGAGTTC  AAGACCAGCC  TGGGCAACAT   180

ATCGAGTCCC  TGCTTTAAAA  AAAAAAAAAA  GGAAGTTTTG  CTGAGAGGCT  AGATGGATTA   240

TGATTTTTGT  TTATTTTTCC  TGTTTATCCA  TATATTATTT  TTCAACAATG  AGTATTGATT   300

ACTTATATAA  TAATTTTAAG  GCTGTACACA  TTGCAGACAG  CACCCCACTG  TTTGAAAAAC   360

TCCTCCTCAG  TAGAACATGG  CAGACCTTCA  TCTTCCTTCC  CTGAACCTTT  TCCAACCTTA   420

GGCTTGCCAT  TCTCCACCAG  TGCTAATGTC  ATGTCTCTTG  AAATCTGTAT  TGAAGTCAGT   480

ATTTCATTCT  TGCCAGTTTC  CACTGTGTGT  TTAAATTTGG  AGTCTGGTGT  CTAGCATTAG   540
```

```
CTGGGGTTGG GGCTTCCACT CCTCTCAGCA TTGGTAAGCC TCCTCACCCA CCCCATCCCA    600
TGTCCAAGAT CACCCAGTTA CACACTTACC ATCTACCCAG TTCATTCACA TCATCAGTCC    660
CAGAGCTGCA GAGATGCTCT TTTTCTACCT CCTACTTCTC TGGCTCTTAG AGAGGCAGCA    720
TGGGATAATG GGCAAGCGA ATAGGGCCTT AAAGTAGAGG GACAAGGGTT CTCTTCCCTA    780
TCTGCCACTT ATTAGCTATG TGACCTCGTG TAAGTCTCTT TTCTTTTTGA GACAGGGTCT    840
CCCTCTGTCA CCTAGGCTGG AGTACAGTGG TATGATCATA GCTCACTGCA GCCTCGAACT    900
CCTGGGCTCA AGCTATCCTT CCACCTTAGC CTTCTGAGCA GCAGGGACTA CAGGCACATG    960
CCACCATGTC CGGCTGATTT ATTTATTTTT ATTTGGGAAG ATGGGGTCT CACTATGTCG    1020
CCCAGGCTGG TCATGAACTC CTGGTCTCAA GCAACCCTCC AACCTTGGAC TCCCAAAGTG    1080
CTGGGATTAC AGGTGTGAGC CCTGGCCTTG CCTCAATTTC CTCATCTGTA AAACGGGGTT    1140
AGTGAAACTC ACATCCTATC AGTGGTTTTG AGGATGGGCC GACTCTTGTA TTGCCTGCTC    1200
TAGTACAATC AGCAGCTAAG GCGGCTCACT TTCCGGCCGT GCTACAATAG GTAAGAACTA    1260
GGATGCTTTA GACGTGTGAC TGGGCAGTGG GAGCCCCTCA CATGATCCCG AGATGCCAGA    1320
CAGTGTCTCT CCGCACAGGG CGTGTGCTGG TCCAGAGGCC CGTTTTCCA GTCGCCCAC     1380
ACCCCGGGTC CGCGATCACG CTCCCCCCAC CCATAGCCGA GCCTGACGCG GCGGTGGCTC    1440
ATGCGCCTTT CCGTCCCAGC CTTTAGCCAC GGACCACACG TCCATCTCA GGCGCCCGC     1500
CCCTCCCCCG CCCCCCGCCC CGGCGCGCC TCCCCAGGCT GCCGGCTCCG GTGTCTGAGC    1560
GGCCGCGCCC GCGAGCCGTG AGCGATGATT GGCTGCGCCA CGGCGGCGGG CGGTCCGTGG   1620
GCGCACACAC CCTCCCCGCG CAGCCAATGG GCGTGCGCAC GTCACTGATC CGGAGGCCCG   1680
CGGGCCGGCA GCCCCTCAAT AAGCCACATT GTTGCATGAA ACTCCGGCGC AGGAGTCCCG   1740
GGCTGCCGCT GGCAACATCG TGTCACCCAG CTAAGAAAAT CCGCGGGCCC GAGCCACGCG   1800
CCTGTGAATC GGAGAGGTCC CACTGCCCGA GTGGAGCCGG GCTGAGATTC TTCTCAAGTT   1860
GAGCCTCAGT GATCCTGTGG CCGAAGTTAG CGCCTTGACG TGGGACAACC GGACACGTCG   1920
CCAGGAGAGA ACTGAGGCGC CTTCTAGCAG TTGTGACGCC AAAATCACGT CTCCGGAGAC   1980
CCGCGCCCTC CGCCAGCCGG GCGCACCCTC GCCGGTAGCC TTCTTTGTGC GCCGTCCGGA   2040
CTCCCAGCTC CCGGCCCGGC AGCCGAGCCC CAGCACAAAG CAGTCGGACC GCGCCGCCCG   2100
CCTCCCCTCT CGCGTCTCCG CCTCGGTTTC CCAACTCTGC GCCGTCGGGC CGCGGCAGGA   2160
TGATTGCCTC GCATCTGCTT GCCTACTTCT TCACGGAGCT C                       2201
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CAGCACAAAG CAGTCGGACC                                                 20
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GAGCTCCGAG AAGAAGTAGG                                                        20
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:4:

```
GCCGCTGGCA ACATCGTGTC                                                        20
```

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:5:

```
CCGCTCGAGT GCCGCGGCCC GACGGCG                                                27
```

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:6:

```
CGCGGATCCT GCCGCGGCCC GACGGCG                                                27
```